(12) United States Patent
Brody

(10) Patent No.: US 10,114,216 B2
(45) Date of Patent: Oct. 30, 2018

(54) MINIMALLY INVASIVE LENS CLEANER

(71) Applicant: Fredrick Brody, Bethesda, MD (US)

(72) Inventor: Fredrick Brody, Bethesda, MD (US)

(73) Assignee: C-CLEAR LLC, Midvale, UT (US)

( * ) Notice: Subject to any disclaimer, the term of this patent is extended or adjusted under 35 U.S.C. 154(b) by 0 days.

(21) Appl. No.: 14/807,795

(22) Filed: Jul. 23, 2015

(65) Prior Publication Data

US 2016/0022367 A1 Jan. 28, 2016

Related U.S. Application Data

(60) Provisional application No. 62/028,766, filed on Jul. 24, 2014.

(51) Int. Cl.
| | | |
|---|---|---|
| *G02B 27/00* | (2006.01) | |
| *A61B 1/12* | (2006.01) | |
| *A61B 1/253* | (2006.01) | |
| *A61B 90/70* | (2016.01) | |
| *G02B 23/24* | (2006.01) | |

(52) U.S. Cl.
CPC .......... *G02B 27/0006* (2013.01); *A61B 1/126* (2013.01); *A61B 1/127* (2013.01); *A61B 1/253* (2013.01); *A61B 90/70* (2016.02); *G02B 23/24* (2013.01)

(58) Field of Classification Search
CPC ....... A61B 1/126–1/127; A61B 1/1253; A61B 19/34; A61B 1/00131; A61B 1/313; A61B 2017/3437; A61B 10/04
USPC ......................................... 600/121–125, 169
See application file for complete search history.

(56) References Cited

U.S. PATENT DOCUMENTS

| | | | | | |
|---|---|---|---|---|---|
| 3,809,072 A | * | 5/1974 | Ersek | ................. | A61B 1/00142 385/117 |
| 5,172,683 A | * | 12/1992 | West | ......................... | F24J 1/00 126/263.05 |
| 5,295,952 A | * | 3/1994 | Pietrafitta | .............. | A61B 10/04 604/1 |
| 5,339,800 A | * | 8/1994 | Wiita | ................. | A61B 1/00091 600/109 |
| 5,351,675 A | * | 10/1994 | Brodsky | ................ | A61B 1/127 126/263.08 |
| 5,363,843 A | * | 11/1994 | Daneshvar | ......... | A61B 1/00142 128/897 |
| 5,382,297 A | * | 1/1995 | Valentine | ............... | A61B 1/122 134/15 |
| 5,392,766 A | * | 2/1995 | Masterson | ........... | A61B 1/0008 15/244.1 |
| 5,400,767 A | * | 3/1995 | Murdoch | ........... | A61B 1/00135 600/157 |

(Continued)

*Primary Examiner* — Matthew J Kasztejna
(74) *Attorney, Agent, or Firm* — Finnegan, Henderson, Farabow, Garrett & Dunner, LLP

(57) ABSTRACT

A device for cleaning the lens of a scope is disclosed. The device comprises a sleeve including an inner surface configured to engage a medical device; and a pad secured around the sleeve and configured to wipe the lens of the scope. While a cleaning fluid can be applied to the pad, the device does not require nor does it contain a reservoir for cleaning solution. A method of cleaning a lens of a scope using such a device is also disclosed. A lens cleaning system comprising the device positioned on a medical device, such as an elongated surgical instrument, is also disclosed.

20 Claims, 4 Drawing Sheets

(56) References Cited

U.S. PATENT DOCUMENTS

| | | | | |
|---|---|---|---|---|
| 5,480,302 | A * | 1/1996 | Fife | A61C 1/16 206/438 |
| 5,514,084 | A * | 5/1996 | Fisher | A61B 1/126 600/157 |
| 5,549,543 | A * | 8/1996 | Kim | A61B 1/3132 219/429 |
| 5,651,757 | A * | 7/1997 | Meckstroth | A61B 1/127 600/101 |
| 5,910,106 | A * | 6/1999 | Morgan | A61B 1/00131 126/263.05 |
| 6,234,635 | B1 * | 5/2001 | Seitzinger | A61B 1/127 359/512 |
| 6,277,066 | B1 * | 8/2001 | Irwin | A61B 8/4281 600/115 |
| 6,305,536 | B1 * | 10/2001 | Tanaka | A61B 1/00142 206/316.2 |
| 6,530,881 | B1 * | 3/2003 | Ailinger | A61B 1/00142 600/114 |
| 7,021,064 | B2 * | 4/2006 | Wohland | A45D 34/00 126/263.07 |
| 7,080,641 | B2 * | 7/2006 | Gomez | A61F 7/0085 126/263.01 |
| 7,591,782 | B2 * | 9/2009 | Fujikura | A61B 1/00082 600/115 |
| 8,267,896 | B2 * | 9/2012 | Hartoumbekis | A61B 1/126 604/167.01 |
| 8,353,819 | B2 * | 1/2013 | Okoniewski | A61B 1/00142 600/121 |
| 8,721,529 | B2 * | 5/2014 | Hess | A61B 17/320092 600/127 |
| 8,747,304 | B2 * | 6/2014 | Zeiner | A61B 1/00087 600/104 |
| 8,926,507 | B2 * | 1/2015 | Kleyman | A61B 17/3423 600/204 |
| 9,060,676 | B2 * | 6/2015 | Blackhurst | A61B 1/0008 |
| 9,078,694 | B2 * | 7/2015 | Hartoumbekis | A61B 1/126 |
| 9,232,935 | B2 * | 1/2016 | Brand | A61B 1/00131 |
| 2002/0022762 | A1 * | 2/2002 | Beane | A61B 1/122 600/101 |
| 2009/0105543 | A1 * | 4/2009 | Miller | A61B 1/126 600/155 |
| 2013/0041230 | A1 * | 2/2013 | Hartoumbekis | A61B 1/126 600/205 |
| 2013/0085337 | A1 * | 4/2013 | Hess | A61B 90/70 600/157 |
| 2014/0094650 | A1 * | 4/2014 | Schaning | A61B 1/313 600/104 |

* cited by examiner

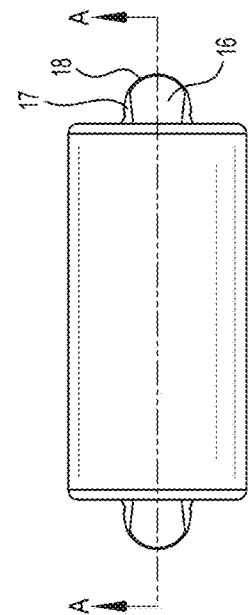
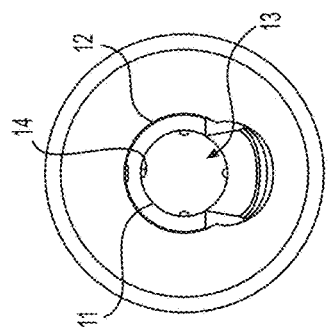
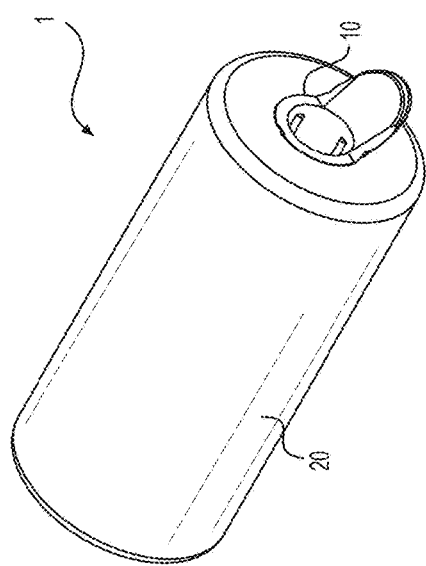
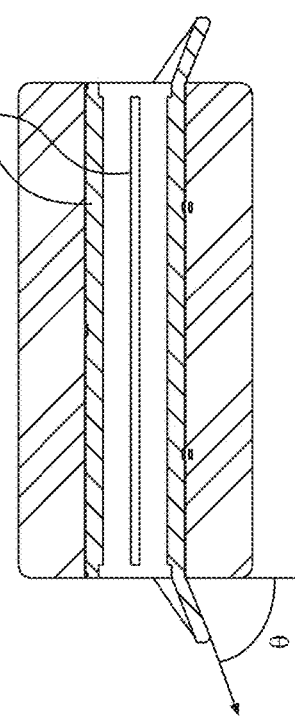
FIG. 1B
FIG. 1D
FIG. 1A
FIG. 1C

MINIMALLY INVASIVE LENS CLEANER

PRIORITY

This application claims priority to U.S. provisional patent application No. 62/028,766 filed on Jul. 24, 2014, which is incorporated herein by reference in its entirety.

TECHNICAL FIELD

The present disclosure relates generally to a device used in surgical and medical procedures and, more particularly, to a device for cleaning a lens attached to a medical device during minimally invasive procedures.

BACKGROUND

Minimally invasive and endoscopic procedures continue to be popular among surgeons, and the number of procedures is expected to steadily increase in the coming years. Compared to open surgeries, minimally invasive procedures allow patients to heal faster, with a shorter convalescence period and decreased risk for wound complications. However, minimally invasive procedures introduce a number of difficulties due to limited access and visibility inside the body cavity. The procedures typically involve making small incisions to introduce equipment and scopes into the body cavity in order to perform complicated medical procedures, such as ligating, cutting, clamping, suturing, and/or repairing tissue. Consequently, these difficulties often require skilled surgeons and excellent visualization obtained through a scope.

One of the most common problems that prolongs the minimally invasive procedure is associated with maintaining continued visibility. After inserting the scope into the body, the lens can become obstructed due to smudging, condensation, and/or direct contact with body tissue and fluids. In order to provide the surgeon with a clear view, the scope often needs to be removed from the body cavity, cleaned, and then reinserted. During some procedures, it is not uncommon to remove and clean the scope 10-20 times, substantially lengthening the procedure and possibly leading to other complications. Thus, there is a need of a method and device to clean the lens of a scope that does not require removing it from a body cavity.

The minimally invasive lens cleaner of the present disclosure solves one or more of the problems set forth above and/or other problems in the art.

SUMMARY

In one aspect, the present disclosure is directed to a device for cleaning a lens of a scope. In one embodiment, the device comprises a sleeve including an inner surface configured to engage an elongated medical device; and a pad secured around the sleeve and configured to wipe the lens of the scope. The device does not include a reservoir or container for holding a cleaning solution.

In another aspect, the present disclosure is directed to a method of cleaning a lens of a scope, the method comprising: positioning a device for cleaning the lens around a medical device; inserting the elongated medical device into a body cavity; and contacting the lens with the pad to remove a substance from the lens. In one embodiment, the device comprises: a sleeve including an inner surface configured to engage the elongated medical device; and a pad secured around the sleeve and configured to wipe a lens of a scope.

In yet another embodiment there is disclosed a cleaning system, comprising: a medical device; and a lens cleaner comprising: a sleeve comprising an inner surface engaging the medical device; and an absorbent pad secured around the sleeve and configured to wipe a lens of a scope.

It is to be understood that both the foregoing general description and the following detailed description are exemplary and explanatory only and are not restrictive of the invention, as claimed.

BRIEF DESCRIPTION OF THE DRAWINGS

The accompanying figures, which are incorporated in and constitute a part of this specification, illustrate several embodiments of the invention and together with the description, serve to explain the principles of the invention.

FIG. 1A is an isometric illustration of an exemplary disclosed lens cleaner;

FIG. 1B is a top-view illustration of the lens cleaner of FIG. 1A;

FIG. 1C is a cross-sectional view along the Line A-A of FIG. 1B;

FIG. 1D is an end-view illustration of the lens cleaner of FIG. 1A;

DETAILED DESCRIPTION

Figure 2:
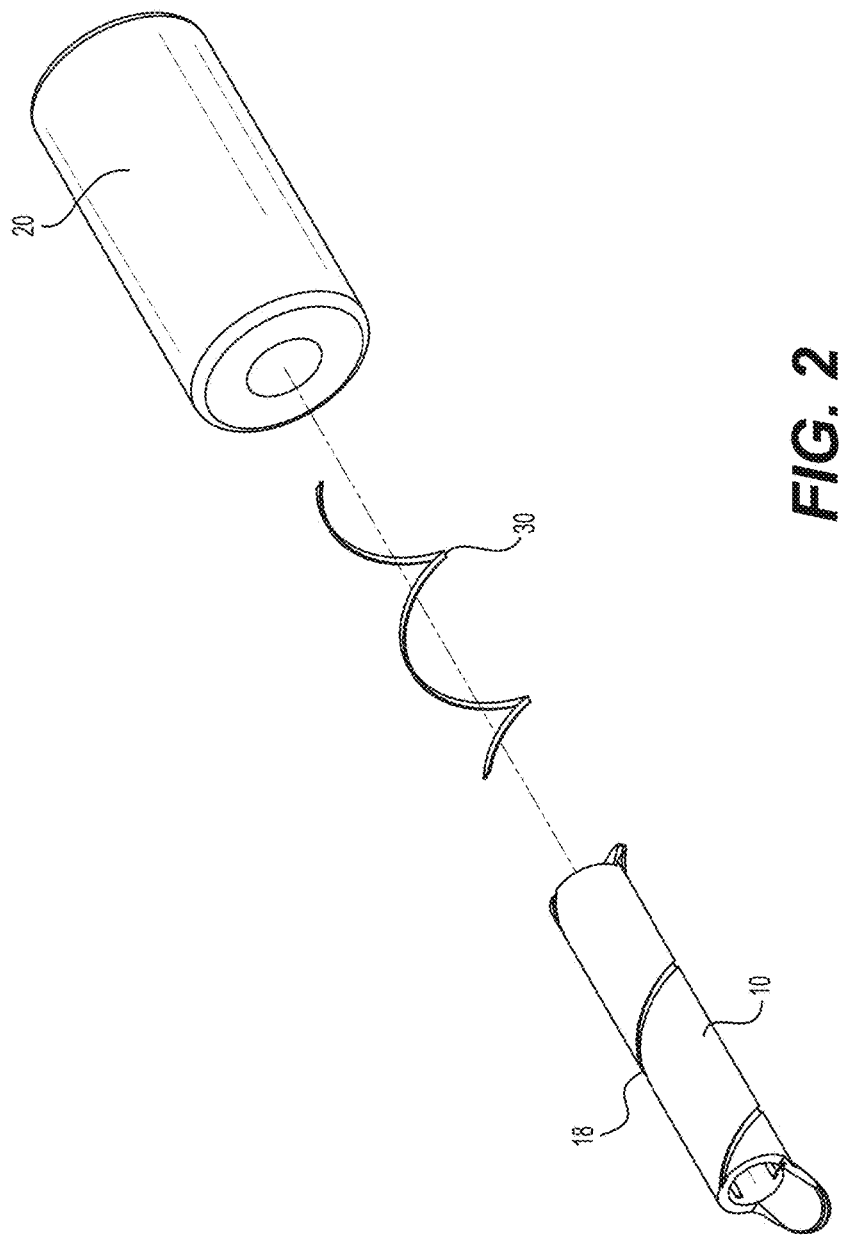
FIG. 2 is an exploded view of an exemplary disclosed lens cleaner.

There is disclosed in one embodiment, a minimally invasive lens cleaner that comprises (1) a sleeve that slides over and connects to a medical instrument, and (2) a soft surface that is attached to the sleeve for the purpose of cleaning a lens. The first component mechanically mates, slides, or fits onto the medical instrument. This embodiment wraps around the medical device and held there by friction. The attached figures provide more detail below. The soft surface attached to the sleeve provides a cushioned landing zone for the minimally invasive lens to wipe during a surgical procedure without removing the device the body. The soft surface may be angled or circular. The soft surface may be made of sponge, foam or cloth like material. A wide range of materials may be used as a soft surface to wipe and clean the lens.

The Inventor has discovered that the device according to the present disclosure does not contain, nor does it require a fluid retention channel or chamber. Rather, the device described herein relates to an instrument cleaning apparatus, which facilitates the cleaning of a scope inserted through a sealed portal during a surgical procedure by providing a device that functions without a related fluid retention chamber and within the operating cavity so that the surgical instrument need not be removed therefrom.

FIGS. 1A-D illustrate an exemplary disclosed lens cleaner 1. Lens cleaner 1 may include a sleeve 10 configured to engage an elongated medical device and a pad 20 positioned around sleeve 10 configured to wipe and clean a scope lens.

Sleeve 10 may have a number of different configurations to releasably secure pad 20 onto an outer surface of the elongated medical device. As depicted in FIGS. 1A-D, sleeve 10 may have an inner wall 11 and an outer wall 12 that define a tubular configuration. Sleeve 10 may define a lumen 13 configured to receive the elongated medical device and have a substantially cylindrical cross-section. Alternatively, sleeve 10 may be provided with other cross-sections, such as square, rectangular, triangular, and oval, depending on the shape of the elongated medical device.

Sleeve 10 may comprise any number of flexible or rigid materials to prevent movement (e.g., translation and/or rotation) of pad 20 relative to the elongated medical device. For example, sleeve 10 may comprise biocompatible materials, such as elastomers, rubbers, plastics, polymers, and metals. In one embodiment, sleeve 10 may include a silicone elastomer that provides a soft, flexible material with a high coefficient of friction for gripping the outer surface of the elongated medical device. In another embodiment, sleeve 10 may include a more rigid polymeric material, such as polyethylene, that may be configured to interlock with the outer surface of the elongated medical device.

As depicted in FIGS. 1C and 1D, sleeve 10 may include one or more protrusions 14 extending from inner wall 11 into lumen 13 to enhance the grip of the elongated medical device. Protrusions 14 may have a number of different configurations. In one embodiment, protrusions 14 may include one or more elongated ridges extending substantially the entire length of sleeve 10 and positioned equidistance around lumen 13, as shown in FIG. 1B. In another embodiment, protrusions 14 may include one or more ring-shaped ridges extending around lumen 13 at discrete locations along the longitudinal axis of sleeve 10 (not shown). It is also contemplated that protrusions 14 may have other configurations, such as being helical, cross-hatched, and cobblestoned.

Protrusions 14 may be configured to engage a uniform outer surface of the elongated medical device or to mate with corresponding recesses. In embodiments where sleeve 10 includes a flexible material, such as a silicone elastomer, protrusion 14 may provide a surface with a high coefficient of friction for gripping the outer surface of the medical device. The flexibility of the silicone elastomer may allow sleeve 10 to slide along the outer surface of the elongated medical device and the high coefficient of friction would prevent relative movement once in place. In embodiments where sleeve 10 is a more rigid material, such as polyethylene, protrusions 14 may be sufficiently flexible to slide along the elongate medical device but may be sufficiently rigid to interlock with corresponding recesses of the outer surface of the elongated medical device. In this embodiment, protrusions 14 may generate a tactile and/or audible snapping to ensure that lens cleaner 1 is secured to the elongated medical device.

Lens cleaner 1 may further include one or more tabs 16 formed on a longitudinal end of sleeve 10. Tabs 16 may be embodied as angled extensions integrated with longitudinal ends of sleeve 10. As shown FIG. 1C, tabs 16 may extend at an angle, θ, relative to outer surface 12 of sleeve 10. The angle, θ, may be between about 50° and 80° degrees (e.g. about) 68° to provide a number of advantages, as discussed below. In other embodiments, the angle, θ, may be between about 45° and 80° degrees. As illustrated in FIG. 1B, tabs 16 may also include side walls 17 that diverge and narrow to provide an enlarged lip 18 at its longitudinal end. Tabs 16 may additionally define a concave inner surface having a curvature approximating the curvature of sleeve 10.

Tabs 16 may be configured to provide an enlarged surface that guides the elongated medical device into the lumen of sleeve 10. For example, the concavity and angle, θ, of tabs 16 facilitate the threading of the elongated medical device through lumen 13. Tabs 16 may also facilitate insertion and removal of lens cleaner by providing a surface that can be grasped and manipulated. Like sleeve 10, tab 16 may be formed of a soft, flexible material with a high coefficient of friction providing a grip for grasping and pulling sleeve 10 along the length of the elongated medical device. This is especially advantageous by facilitating removal of lens cleaner 1 without contacting pad 20, which may be saturated with body fluids. These features allow the lens cleaner 1 to be threaded or removed from the elongated medical device, even when the elongated medical device is in the body cavity and the surgeon lacks dexterity. Tabs 16 may be formed integral with sleeve 10 or may be a separate structure. Tabs 16 may include plastic, metal, or silicone, and may be embodied as a loop of suture material (not shown).

Pad 20 may provide a cushioned surface to clean the scope lens during a surgical procedure without removing the device from the body cavity. Pad 20 may include a number of different absorbent materials configured to absorb fluid and tissue without scratching the lens. For example, pad 20 may include materials such as a sponge, a foam, a gauze, or a fabric. The absorbent material may absorb fluids or materials without the need of fluid retention channels or chambers. Pad 20 may have a substantially cylindrical cross-section circumventing sleeve 10, which facilitates the contact between the scope lens and pad 20, without having to rotate the medical device. Pad 20 may be provided with rounded or chamfered corners, as depicted in FIG. 1A. It is also contemplated that pad 20 may have an irregular or a polygonal cross-section, such as rectangular, hexagonal, or octagonal (not shown). Pad 20 may extend substantially the entire longitudinal length of sleeve 10, and pad 20 may be secured to the sleeve 10 with an adhesive, weld, or the like.

Lens cleaner 1 may have a variety of dimensions configured to fit around the elongated medical device. Lens cleaner 1 may have a total longitudinal length between about 40-55 mm (e.g. about 48 mm) and a width (e.g. outer diameter, when pad 20 has a circular cross-section) between about 15-20 mm (e.g. about 18 mm). Pad 20 may have a longitudinal length between about 35-45 mm (e.g. about 38 mm), and tabs 16 may each have a length between about 2-8 mm (e.g. about 5 mm). Lumen 13 may have a width (e.g. diameter, when sleeve 10 has a circular cross-section) between about 5-10 mm (e.g. about 8 mm).

Pad 20 may be used with or without a cleaning solution. In one embodiment, pad 20 may be soaked or impregnated with a cleaning solution prior to inserting lens cleaner 1 into the body cavity. It is contemplated that the cleaning solution may include a number of different substances, including a saline solution. In another embodiment, pad 20 may be inserted into the body cavity without applying any cleaning solution. In this embodiment, pad 20 may be maintained in the body cavity for a length of time (e.g., a couple of minutes) to absorb moisture from the body cavity prior to any contact with a medical device. In yet another embodiment, pad 20 may contact a medical device in a dry state. However, in any case, lens cleaner 1 functions without a related fluid retention channel or chamber and does not need to be removed from the body cavity during use.

FIG. 2 illustrates an exploded view of an exemplary embodiment of lens cleaner 1. As illustrated, a radiopaque strip 30 may be sandwiched between sleeve 10 and pad 20 to allow the surgeon to visualize the positioning and orientation of lens cleaner 1 when positioned within the body cavity. Outer wall 12 of sleeve 10 may include a groove 18 configured to receive strip 30. Groove 18 may have a width and depth substantially equal to or greater than the width and depth of strip 30 to allow strip 30 to be recessed into the outer wall 12 of sleeve 10. This positioning of the strip 30 allows the pad to maintain an unobstructed absorbent surface and prevents any scratching from contact between strip 30 and the lens of the scope. As depicted in FIG. 2, strip 30 and groove 18 may each have a helical configuration extending circumferentially around sleeve 10. The helical configuration of strip 30 allows visualization of lens cleaner 1 at any angle. However, it is also contemplated that strip 30 may have other configurations such as being linear or serpentine (not shown). In another embodiments, strip 30 may be embedded within pad 20. In other embodiments, strip 30 may be formed from radiopaque markings or dyes applied to sleeve 10 and/or pad 20. Additional strips 30 may be provided to allow the surgeon to enhance visualization of lens cleaner 1 through X-ray, fluoroscopy, MRI, and/or CT scan imaging.

Figure 3:
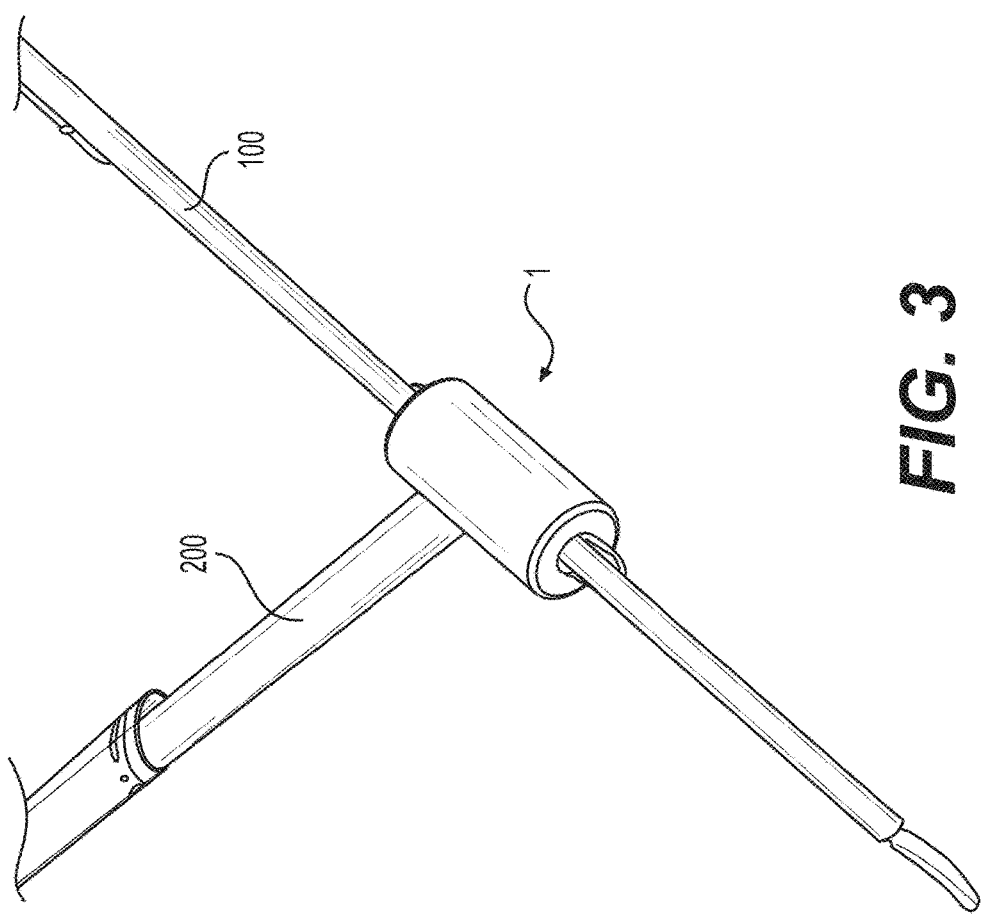
FIG. 3 is an illustration of a lens cleaning system used in conjunction with an scope.

FIG. 3 illustrates a contemplated lens cleaning system for use in a method of cleaning a scope 200. The lens cleaner system may include lens cleaner 1 secured around an elongated medical device 100. Elongated medical device 100 may include any tool, device, or instrument used in conjunction with a scope. For example, elongated medical device 100 may include at least one of forceps, a trocar, cautery, a suture passer, a clip applier, a clamp, and a suction tube. Elongate medical device 100 may also embody a catheter or sheath that houses a medical instrument. Elongate medical device 100 may be disposable or non-disposable.

In some embodiments, lens cleaner 1 may be removably secured to elongated medical device 100 by way of a frictional or interlocking engagement, as previously discussed. In another embodiment, lens cleaner 1 may be permanently secured to elongated medical device 100. For example, lens cleaner 1 may be permanently secured to elongated medical device 100 with an adhesive, a weld, or the like in order to prevent detachment. Permanently securing lens cleaner 1 to elongated medical device 100 may obviate the need for sleeve 10, such that pad 20 can be directly secured to elongated medical device 100.

Figure 4:
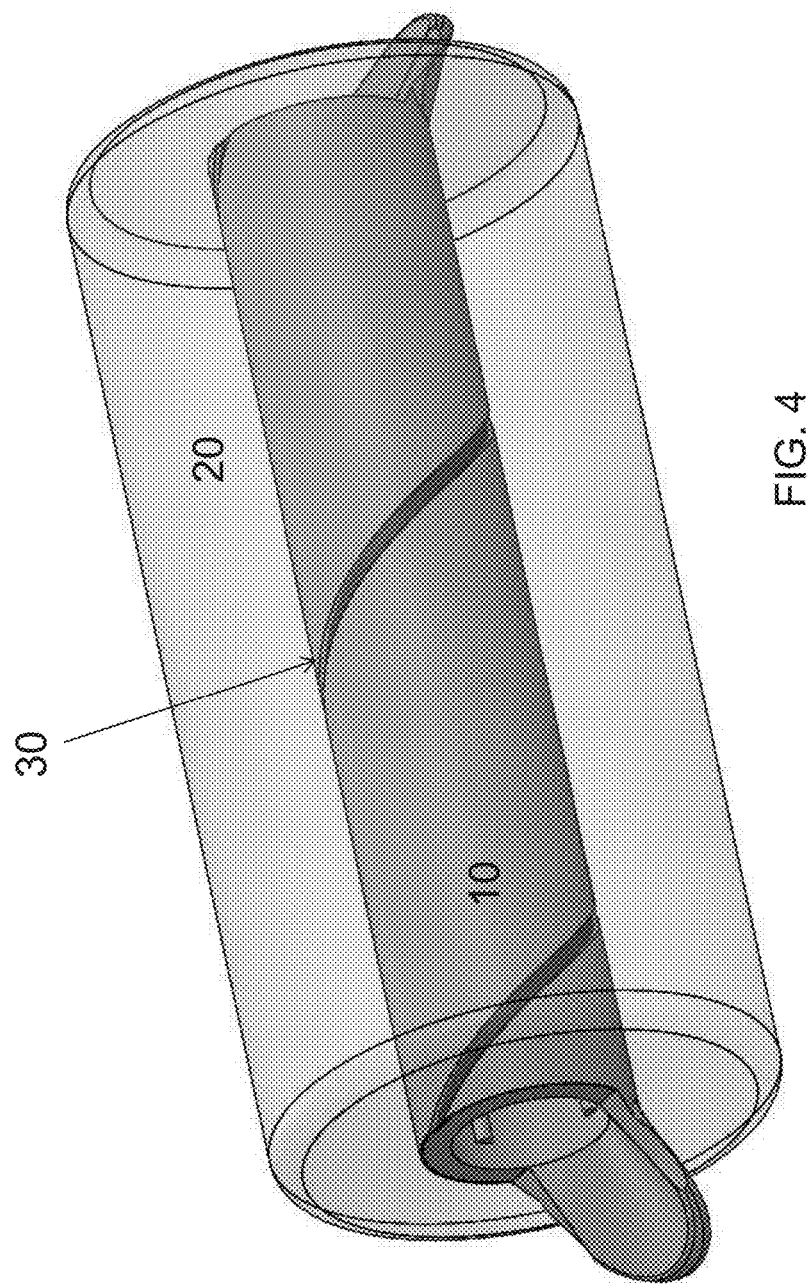
FIG. 4 is an isometric illustration of the exemplary disclosed lens cleaner of FIG. 2.

FIG. 4 illustrates an additional view of an exemplary embodiment of lens cleaner 1 shown in FIG. 2. As illustrated in this embodiment, the radiopaque strip 30 is sandwiched between sleeve 10 and pad 20 to allow the surgeon to visualize the positioning and orientation of lens cleaner 1 when positioned within the body cavity. As depicted in FIG. 4, strip 30 and groove 18 may each have a helical configuration extending circumferentially around sleeve 10. The helical configuration of strip 30 allows visualization of lens cleaner 1 at any angle. However, it is also contemplated that strip 30 may have other configurations such as being linear or serpentine (not shown). Additional strips 30 may be provided to allow the surgeon to enhance visualization of lens cleaner 1 through X-ray, fluoroscopy, MRI, and/or CT scan imaging.

The disclosure also contemplates a method of cleaning a lens of a scope without removing the scope from a body cavity. The method may include positioning lens cleaner 1 around elongated medical device 100. Elongated medical device 100 may be inserted into a body cavity to perform a procedure. At least one of the elongated medical device 100 and scope 200 may be manipulated to contact pad 20 with the lens of scope 200. The soft surface of pad 20 may provide a cushioned landing zone to allow wiping and cleaning of scope 200 without scratching the lens. Advantageously, this procedure may be performed without removing scope 200 from the body cavity or introducing any additional tools into the body cavity to perform the cleaning.

The method of cleaning may be performed during any surgery involving a scope. For example, the method may be applicable to procedures performed laparoscopically, thoracoscopically, endoscopically, and robotically. The method may also be applicable during the course of an open surgery.

The preferred embodiments and examples disclosed in the foregoing specification are used therein as vehicles of description, and not of limitation. There is no intention, in the use of such embodiments and examples to exclude any equivalents of the features shown and described, or portions thereof. It is appreciated that numerous modifications and/or embellishments to these embodiments and examples may be devised by those who are skilled in the art.

Therefore, it is understood that all such modifications and/or embellishments which fall within the spirit and scope of the present disclosure shall be covered by the following enumerated claims.

What is claimed is:

1. A cleaning device for cleaning a lens of an endoscope, the cleaning device comprising:
   a sleeve comprising an inner surface configured to engage a medical device;
   a first tab linearly extending outward from a first longitudinal end of the sleeve at an inclined angle ranging from 45° to 80° with respect to the first longitudinal end, and a second tab linearly extending outward from a second longitudinal end of the sleeve at an inclined angle ranging from 45° to 80° with respect to the second longitudinal end, the first and second longitudinal ends being located on opposite ends of the sleeve, and wherein the first and second tabs are only partially coterminous with the sleeve; and
   a pad secured around the sleeve and configured to wipe the lens, wherein the cleaning device does not include a reservoir for cleaning fluid.

2. The cleaning device of claim 1, wherein the pad includes a substantially cylindrical cross-section circumventing the sleeve, the first and second tabs are symmetric with respect to one another, and the first and second tabs do not extend beyond an external cross-sectional diameter of the cylindrical pad.

3. The cleaning device of claim 1, wherein the first and second tabs each have a concave inner surface and diverging sidewalls.

4. The cleaning device of claim 1, further comprising four protrusions extending along an inner surface of the sleeve, each protrusion being symmetrically spaced along the inner surface of the sleeve relative to the other protrusions.

5. The cleaning device of claim 4, wherein the four protrusions extend substantially the entire length of the sleeve.

6. The cleaning device of claim 4, wherein the at least one protrusion is configured to frictionally engage with the outer surface of the medical device.

7. The cleaning device of claim 1, wherein the pad comprises an absorbent material.

8. The cleaning device of claim 7, wherein the pad comprises at least one of a sponge, a foam, a gauze, and a fabric.

9. The cleaning device of claim 1, wherein the sleeve comprises at least one of an elastomer, a rubber, a plastic, a polymer, and a metal.

10. The cleaning device of claim 9, wherein the sleeve comprises a silicone elastomer.

11. The cleaning device of claim 1, further including a radiopaque strip.

12. The cleaning device of claim 1, wherein the first tab extends outward at about 68° degrees, and the second tab extends outward at about 68°.

13. A method of cleaning a lens of a medical device comprising:
   positioning a cleaning device for cleaning the lens around the medical device;
   inserting the medical device into a body cavity; and
   contacting the lens with the pad to remove at least one substance from the lens selected from condensation, bodily tissues, or bodily fluids, wherein the cleaning device comprises:
   a sleeve including an inner surface configured to engage the medical device;
   a first tab extending outward from a first longitudinal end of the sleeve at an inclined angle ranging from 45° to 80° with respect to the first longitudinal end, and a second tab extending outward from a second longitudinal end of the sleeve at an inclined angle ranging from 45° to 80° with respect to the first longitudinal end, the first and second longitudinal ends being located on opposite ends of the sleeve; and
   an absorbent pad secured around the sleeve and configured to wipe the endoscope,
   wherein the pad includes a substantially cylindrical cross-section circumventing the sleeve, the first and second tabs are symmetric with respect to one another, and the first and second tabs do not extend beyond an external cross-sectional diameter of the cylindrical pad.

14. A system for cleaning a lens of an endoscope, comprising:
   a medical device; and
   a cleaning device comprising:
   a sleeve comprising an inner surface engaging the medical device;
   a first tab extending outward from a first longitudinal end of the sleeve at an inclined angle ranging from 45° to 80° with respect to the first longitudinal end, and a second tab extending outward from a second longitudinal end of the sleeve at an inclined angle ranging from 45° to 80° with respect to the first longitudinal end, the first and second longitudinal ends being located on opposite ends of the sleeve; and
   an absorbent pad secured around the sleeve and configured to wipe the endoscope,
   wherein the pad includes a substantially cylindrical cross-section circumventing the sleeve, the first and second tabs are symmetric with respect to one another, and the first and second tabs do not extend beyond an external cross-sectional diameter of the cylindrical pad.

15. The system of claim 14, wherein the medical device comprises an elongated surgical device.

16. The system of claim 14, wherein the sleeve comprises a silicone elastomer.

17. The system of claim 14, wherein the cleaning device is configured to be removed from the medical device.

18. The cleaning system of claim 14, wherein the medical device comprises forceps, a trocar, cautery, a suture passer, a clip applier, a clamp, a suction tube, a catheter, or sheath.

19. The cleaning system of claim 14, wherein the first tab extends outward at about 68° degrees, and the second tab extends outward at about 68°.

20. A cleaning device for cleaning a lens of an endoscope, the cleaning device not including a reservoir for cleaning fluid, comprising: a sleeve comprising an inner surface configured to engage a medical device; a first tab linearly extending outward from a first longitudinal end of the sleeve at an inclined angle with respect to the first longitudinal end, and a second tab linearly extending outward from a second longitudinal end of the sleeve at an inclined angle with respect to the second longitudinal end, the first and second longitudinal ends being located on opposite ends of the sleeve, and wherein the first and second tabs are only partially coterminous with the sleeve; and a cylindrical pad that circumvents the sleeve, wherein the first and second tabs are symmetric with respect to one another and do not extend beyond an external cross-sectional diameter of the cylindrical pad.

* * * * *